United States Patent [19]

Kasuga et al.

[11] Patent Number: 5,232,878
[45] Date of Patent: * Aug. 3, 1993

[54] PROCESS FOR PRODUCING INORGANIC BIOMATERIAL

[75] Inventors: Toshihiro Kasuga, Akishima; Kiichi Nakajima, Kokubunji, both of Japan

[73] Assignee: Hoya Corporation, Tokyo, Japan

[*] Notice: The portion of the term of this patent subsequent to Oct. 3, 2006 has been disclaimed.

[21] Appl. No.: 537,299

[22] Filed: Jun. 13, 1990

[30] Foreign Application Priority Data

Jun. 30, 1989 [JP] Japan .................................. 1-168869
Jun. 30, 1989 [JP] Japan .................................. 1-168871

[51] Int. Cl.$^5$ .......................... C03C 8/14; C03C 10/02
[52] U.S. Cl. ......................................... 501/10; 501/5; 501/18; 501/32; 501/63; 501/104; 106/35
[58] Field of Search ..................... 501/1, 5, 10, 18, 32, 501/63, 103, 104, 73; 106/35

[56] References Cited

U.S. PATENT DOCUMENTS

| | | | |
|---|---|---|---|
| 4,560,666 | 12/1985 | Yoshida et al. | 501/10 X |
| 4,587,224 | 5/1986 | Keefer et al. | 501/10 X |
| 4,626,392 | 12/1986 | Kondo et al. | 501/10 X |
| 4,643,982 | 2/1987 | Kasuga et al. | 501/10 X |
| 4,652,534 | 3/1987 | Kasuga | 501/10 X |
| 4,871,384 | 10/1989 | Kasuga | 501/5 X |
| 4,897,370 | 1/1990 | Horiguchi et al. | 501/10 X |

FOREIGN PATENT DOCUMENTS

| | | |
|---|---|---|
| 0299342 | 1/1989 | European Pat. Off. |
| 62-173524 | 1/1989 | Japan |
| 62-271677 | 5/1989 | Japan |
| 62-271678 | 5/1989 | Japan |

*Primary Examiner*—Karl Group
*Attorney, Agent, or Firm*—Nixon & Vanderhye

[57] ABSTRACT

The present invention relates to a process for producing an inorganic biomaterial, according to which, there can be obtained an inorganic biomaterial excellent in strength and biocompatibility, having a structure in which portions constituted by crystallized glass or crystals of calcium phosphate excellent in bioactivity are dispersed in a skeleton or matrix constituted by crystals of partially stabilized zirconia and/or alumina showing high strength. Accordingly, the inorganic biomaterial is very useful as biomaterial for artificial bones, dental implants, etc.

9 Claims, 3 Drawing Sheets

PROCESS FOR PRODUCING INORGANIC BIOMATERIAL

BACKGROUND OF THE INVENTION

1. Field of the Invention

The present invention relates to a process for producing an inorganic biomaterial which is useful as an implant material for artificial bones, dental implants, etc.

2. Description of Prior Art

Ceramics have been attracted public attention because ceramics are considered to be biomaterials harmless to a living body compared with polymers and metallic materials. In recent years, ceramics as biomaterials make remarkable progress. Of ceramics, bioactive ceramics capable of forming a chemical bonding with bones are known. Such bioactive ceramics are united with a living body so that there arises no loosening problem. As the bioactive ceramics, there is known crystallized glass obtained by precipitating an apatite crystal [$Ca_{10}(PO_4)_6(O_{0.5}, F)_2$] and a wollastonite crystal [$CaSiO_3$]. However, the bending strength of the crystallized glass shows a value within a range of about 120 to about 230 MPa. To improve the bending strength of the crystallized glass, bioactive materials such as composite crystals of bioactive crystallized glass and zirconia ceramics and composite crystals of bioactive crystallized glass and alumina ceramics have been developed (Japanese Patent Unexamined Publication Nos. Sho-62-231668 and Sho-63-82670). Those composite materials show relatively high bending strength in a range of from 230 to 350 MPa. However, those values are not yet fully satisfactory from the standpoint that the above materials are used in applications such as artificial bones and dental implants. Accordingly, the above materials are subjected to considerable restriction in the purpose of use thereof.

As means for obtaining a material of higher strength, for example, Japanese Patent Unexamined Publication Nos. Hei-1-115360 and Hei-1-115361 disclose a process for producing an inorganic material comprising the steps of mixing glass powder having a particle size smaller than 75 μm, with zirconia or alumina ceramic powder having a particle size smaller than that of the glass powder, molding the resulting mixture into a desired shape, sintering the glass portion of the resulting compact to crystallize it, and sintering the zirconia or alumina ceramic powder portion.

The processes disclosed in the Japanese Patent Unexamined Publication Nos. Hei-1-115360 and Hei-1-115361 are useful in the case where the content of zirconia or alumina ceramic powder is large. However, the processes have the following disadvantages in the case where the content of zirconia or alumina ceramic powder is small. That is, when the glass powder is heated to a temperature enough to sinter the glass powder, (1) the zirconia or alumina ceramic powder may be enveloped in the glass being fluidized, and/or (2) in the positions where the glass is not fluidized well, pores may be formed easily in the vicinity of the interface between the glass and the zirconia or alumina ceramic powder. When the glass is further heated to a temperature enough to crystallize the glass, the fluidization of the glass stops to start crystallization while the states of (1) and (2) are kept as they are with no change. Accordingly, when the zirconia or alumina ceramic powder is heated to a temperature enough to sinter the ceramic powder, the zirconia or alumina ceramic powder cannot be sintered in the positions where the state of (1) exists so that a skeleton of zirconia or alumina ceramics having high strength cannot be formed. Consequently, the resulting composite material cannot show high strength. On the other hand, pores remain in the composite material in the positions where the state of (2) exists, so that the resulting composite material cannot show sufficiently large strength.

Accordingly, in the processes disclosed in the Japanese Patent Unexamined Publication Nos. Hei-1-115360 and Hei-1-115361, the content of crystallized glass contributing to bioactivity must be set to be smaller than the content of zirconia or alumina ceramics as a reinforcement material. In short, bioactivity must be sacrificed. Hence, the processes have a disadvantage in that a considerable time is required for forming a chemical bonding with bones.

As another means for improving the strength of ceramic materials, Japanese Patent Unexamined Publication No. Sho-64-18973 discloses a process in which a ceramic composite material of high strength is prepared by adding partially stabilized zirconia powder with a particle size of 1 μm or less and metal fluoride powder to calcium phosphate powder, such as apatite powder, β-tricalcium phosphate powder and the like, with a particle size of 1 μm or less.

FIG. 5 typically shows the result of observation, through an electron microscope, of the ceramic composite material disclosed in the Japanese Patent Unexamined Publication No. Sho-64-18973. In the drawing, metal fluoride is not shown because the content of metal fluoride is very small. As is clear from FIG. 5, the ceramic composite material has a structure in which fine crystals of calcium phosphate 13 with a particle size of 1 μm or less and fine crystals of partially stabilized zirconia 14 with a particle size of 1 μm or less were mixed together at random. In general, zirconia and calcium phosphate are apt to react with each other. When the two components are mixed together at random as described above, the surface area where the two components are in contact with each other becomes so large that the two components react with each other easily. When calcium phosphate and partially stabilized zirconia react with each other as described above, calcium phosphate and partially stabilized zirconia form solid solutions. As this result, the amount of calcium phosphate is reduced so that excellent biocompatibility cannot be obtained. Further, partially stabilized zirconia is fully stabilized by reaction with calcium phosphate so that the strength and toughness of the ceramic composite material obtained are often unsatisfactory.

SUMMARY OF THE INVENTION

In order to eliminate the defect in the prior art process disclosed in the Japanese Patent Unexamined Publication Nos. Hei-1-115360 and Hei-1-115361, a first object of the present invention is to provide a process for producing an inorganic biomaterial which is excellent in strength and biocompatibility and which is composed of crystallized glass and zirconia and/or alumina ceramics.

In order to eliminate the defect in the prior art process disclosed in the Japanese Patent Unexamined Publication No. Sho-64-18973, a second object of the invention is to provide a process for producing an inorganic biomaterial which is excellent in strength and biocompatibility and which is composed of calcium phosphate and zirconia and/or alumina ceramics.

The first object of the invention has been achieved by a process for producing an inorganic biomaterial, which comprises:

a first step of melting a mixture of glass raw materials and cooling it to thereby prepare glass containing the following components of the following proportions

| CaO | 12 to 56% by weight |
|---|---|
| $P_2O_5$ | 1 to 27% by weight |
| $SiO_2$ | 22 to 50% by weight |
| MgO | 0 to 34% by weight |
| $Al_2O_3$ | 0 to 25% by weight | in a total amount of at least 90%;

a second step of preparing crystallized glass by heat-treating the glass obtained in the first step in a temperature range in which there are precipitated a crystal of apatite and at least one crystal of alkaline earth metal silicate selected from the group consisting of wollastonite, diopside, forsterite, akermanite and anorthite;

a third step of preparing mixture powder by mixing the crystallized glass obtained by the second step with partially stabilized zirconia powder and/or alumina powder while grinding the crystallized glass or after grinding the crystallized glass; and a fourth step of preparing an inorganic biomaterial of a ceramics/crystallized glass composite by molding the mixture powder obtained by the third step into a desired shape and then heat-treating the resulting molding in a temperature range in which the partially stabilized zirconia and/or alumina powder is sintered.

Hereinafter, the aforementioned process for producing an inorganic biomaterial is called the process according a first aspect of the present invention.

The second object of the present invention has been achieved by a process for producing an inorganic biomaterial, which comprises:

a first step of sintering a crystal of calcium phosphate at a temperature in a range of from 800° to 1400° C. to thereby prepare a calcium phosphate crystal sintered body;

a second step of grinding the sintered body obtained in the first step to thereby prepare powder of the sintered body, and, at the same time of or after preparation of the powder of the sintered body, mixing the prepared powder of the sintered body with partially stabilized zirconia powder and/or alumina powder to thereby prepare mixture powder; and a third step of molding the mixture powder obtained in the second step into a desired shape and heat-treating the resulting molding in a temperature range in which the partially stabilized zirconia and/or alumina powder is sintered.

Hereinafter, the process for producing an inorganic biomaterial described directly above is call the process according a second aspect of the present invention.

DETAILED DESCRIPTION OF THE PREFERRED EMBODIMENTS

Figure 1:
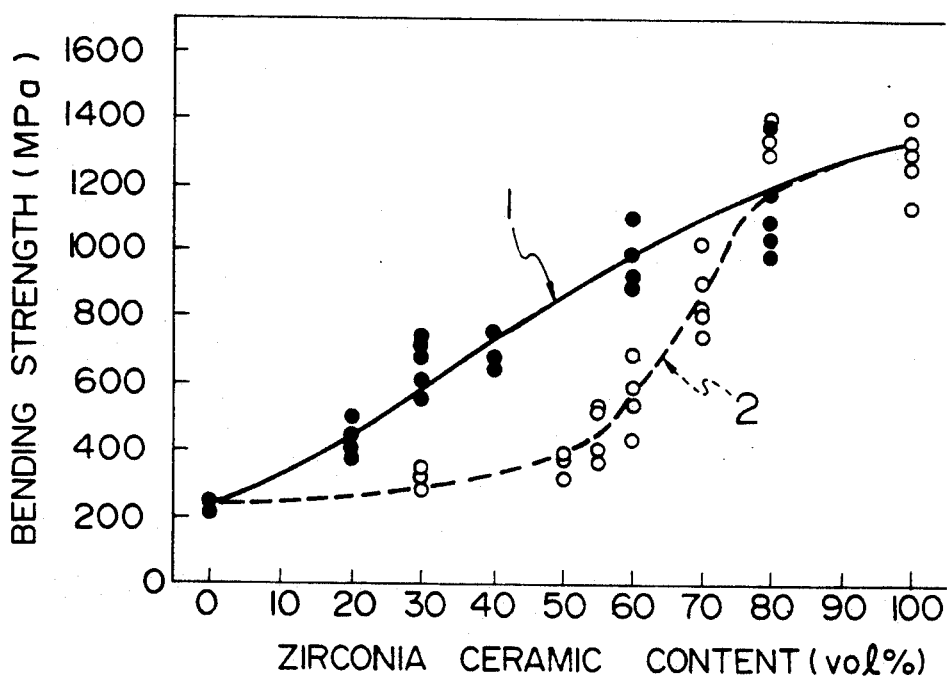
FIG. 1 is a graph showing the relationship between zirconia ceramic content (percentage by volume) and bending strength, of a zirconia ceramics/crystallized glass composite obtained according to the first aspect of the invention.

The process for producing an inorganic biomaterial according to the first aspect of the invention will be explained successively the step by the step.

The first step is of melting a mixture of glass raw materials and cooling it to thereby prepare glass containing the following components of the following proportions

| CaO | 12 to 56% by weight |
|---|---|
| $P_2O_5$ | 1 to 27% by weight |
| $SiO_2$ | 22 to 50% by weight |
| MgO | 0 to 34% by weight |
| $Al_2O_3$ | 0 to 25% by weight | in a total amount of at least 90%.

The proportions of the components in the glass obtained in the first step are restricted quantatively as described above. The reason is as follows.

When CaO content is less than 12%, not only the amount of the precipitated crystals of apatite $[Ca_{10}(PO_4)_6(O_{0.5},F)_2]$ becomes very small but the resulting glass has a high tendency of devitrification. When the CaO content is more than 56%, the resulting glass has a high tendency of devitrification. Accordingly, the CaO content is restricted to fall within a range of from 12 to 56%. When the $P_2O_5$ content is less than 1%, the resulting glass has a high tendency of devitrification. When the content is more than 27%, the total amount of the precipitated crystals of alkaline earth metal silicates such as wollastonite $[CaOSiO_2]$, diopside $[CaO\ MgO\ 2SiO_2]$, forsterite $[2MgO\ SiO_2]$, akermanite $[2CaO\ MgO\ 2SiO_2]$, anorthite $[CaO\ Al_2O_3\ 2SiO_2]$ and the like becomes small. Therefore, the $P_2O_5$ content is restricted to 1-27%. When the $SiO_2$ content is less than 22%, the total amount of the precipitated crystals of alkaline earth metal silicates becomes small. When the content is more than 50%, the resulting glass tends to be devitrified. Hence, the $SiO_2$ content is restricted to 22-50%. Though MgO is not an essential component, it is used for precipitating crystals of diopside, forsterite and akermanite. When the MgO content is more than 34%, not only the amount of precipitated crystals of apatite becomes small but the glass tends to be devitrified. Therefore, the MgO content is restricted to 34% or less. $Al_2O_3$ is not an essential component, either. It is used for precipitating crystals of anorthite. When the $Al_2O_3$ content is more than 25%, not only the amount of precipitated crystals of apatite becomes small but the glass tends to be devitrified. Therefore, the $Al_2O_3$ content is restricted to 25% or less.

In the invention, the glass can contain, in addition to the above five components, at least one component selected from $K_2O$, $Li_2O$, $Na_2O$, $TiO_2$, $ZrO_2$, SrO, $Nb_2O_5$, $Ta_2O_5$, $B_2O_3$, $Y_2O_3$ and fluorine ($F_2$) (all of which give no harm to human bodies) in a total amount of 10% or less. When the total amount of these optional components is more than 10%, the amounts of precipitated crystals of apatite and alkaline earth metal silicates (wollastonite, diopside, forsterite, akermanite, anorthite) decrease in some cases. Therefore, the total amount of these optional components is restricted to 10% or less. When the fluorine content (calculated as $F_2$) is more than 5%, the resulting glass is easily devitrified. When the $Y_2O_3$ content is more than 5%, the amounts of precipitated crystals of apatite and alkaline earth metal silicates decrease. Accordingly, the fluorine content and the $Y_2O_3$ content are each restricted to 5% or less.

In the first step, the glass having the aforementioned composition is prepared by melting a batch of glass raw materials by heating metal oxides per se and corresponding carbonates, phosphates, hydrates, fluorides, etc. to 1300° C. or more and then cooling the batch rapidly.

The second step is of preparing crystallized glass by heat-treating the glass obtained in the first step in a temperature range in which there are precipitated a crystal of apatite and at least one crystal of alkaline earth metal silicate selected from the group consisting of wollastonite, diopside, forsterite, akermanite and anorthite. When the glass obtained in the first step is heated from room temperature to a temperature higher than a glass transition point, the glass is easily fluidized to start sintering of the glass. When the glass is further heated, crystallization of the glass starts. In general, fully crystallized glass cannot be sintered any more even if the glass is heated again. These phenomena can be observed from the differential thermal analysis of glass. In general, the degree of sintering of the glass can be controlled by controlling the degree of progress of crystallization based on heat-treating temperature and time. In the second step, it is preferable that the glass is crystallized so fully as not to be sintered again. The reason is that the sintering property of zirconia and/or alumina ceramic powder in the fourth step is utilized fully.

For example, the temperature range in which an apatite crystal and at least one crystal of an alkaline earth metal silicate are precipitated can be obtained from the differential thermal analysis of glass. That is, X-ray diffraction data of glass powder heat-treated at temperature with various heating peaks in the differential thermal analysis curve are analyzed to identify precipitated crystals corresponding to the heating peaks, and the temperature range from the start of heat generation to its completion in the differential thermal analysis curve is defined as the temperature ranges in which the crystals are precipitated. For example, the temperature range in which the aforementioned crystals are precipitated is from 750° to 1260° C. In the second step, crystals of α- or β-tricalcium phosphate [$Ca_3(PO_4)_2$], in addition to the aforementioned crystals, are precipitated in some cases.

The third step is of preparing mixture powder by mixing the crystallized glass obtained by the second step with partially stabilized zirconia powder and/or alumina powder while grinding the crystallized glass or after grinding the crystallized glass. The grinding of the crystallized glass is conducted by a known means using a ball mill or the like. It is preferable that the particle size of the resulting crystallized glass powder is 500 μm or less. The reason is as follows. When particles larger than 500 μm exist in the resulting crystallized glass powder, the particle size of the crystallized glass powder cannot be reduced to a desired value of 75 μm or less by mixing and grinding together with zirconia and/or alumina ceramic powder by using a known means using a ball mill or the like. The desired value of the particle size is 75 μm or less. The reason is as follows. A crystallized glass portion having a larger particle size than 75 μm is, in most cases, so defective that the mechanical strength of the finally produced inorganic biomaterial consisting of the ceramic/crystallized glass composite cannot be taken to a large value.

Although the above description is made about the case where the crystallized glass is ground and then the resulting crystallized glass powder is mixed with zirconia and/or alumina ceramic powder, the invention can be applied to the case where the grinding of the crystallized glass and the mixing of the crystallized glass with zirconia and/or alumina ceramic powder may be carried out simultaneously by using a known means using a ball mill or the like. Also in this case, it is preferable that the particle size of the crystallized glass obtained is 75 μm or less.

The zirconia ceramic powder mixed into the crystallized glass in this step is constituted by partially stabilized zirconia. The partially stabilized zirconia is prepared to attain high strength and high toughness by utilizing the stress-induced transformation (martensitic transformation) of the tetragonal zirconia crystal particles ordinarily containing at least one component selected from $Y_2O_3$, MgO, CaO and $CeO_2$ as solid solution. Accordingly, the partially stabilized zirconia has high strength of 1000 to 2000 MPa. By mixing α-alumina to the partially stabilized zirconia and sintering the resulting mixture further densely, zirconia-alumina composite ceramic showing very high strength of 1500 to 2400 MPa due to the micro-crack toughening effect could be fabricated. The partially stabilized zirconia powder containing α-alumina can be used as the zirconia ceramic powder used in the process according to the first aspect of the invention. To stabilize zirconia partially, at least one member selected from the following group can be added to $ZrO_2$:

| | |
|---|---|
| $Y_2O_3$ | 1.5–5 mol |
| MgO | 7–10 mol |
| CaO | 7–10 mol |
| $CeO_2$ | 4–15 mol |
| ($ZrO_2$ | 100 mol) |

In the case where α-alumina is added to the partially stabilized zirconia, the weight ratio of partially stabilized zirconia to α-alumina is preferably in a range of from 95:5 to 10:90. The reason is as follows. When the partially stabilized zirconia content is less than 10%, the effect of reinforcement by utilizing the stress-induced transformation of zirconia is so unsatisfactory that the strength cannot be improved effectively. When the α-alumina content is less than 5%, the effect of α-alumina is very small. The more preferred range of the weight ratio is in a range of from 95:5 to 20:80.

It is preferable that the zirconia powder mixed with the crystallized glass has a smaller particle size than that of the crystallized glass powder. The reason is as follows. When the particle size of the zirconia ceramic powder is larger than the particle size of the crystallized glass powder, pores are formed easily in the vicinity of the boundary between the zirconia particles and the crystallized glass to make it difficult to prepare a zirconia ceramic/crystallized glass composite of high mechanical strength. Zirconia ceramic fine powder with the particle size of 1 μm or less can be obtained according to a wet method such as a coprecipitation method, a hydrolysis method, an alkoxide method or the like. Accordingly, it is desirable that zirconia powder obtained as described above is used.

Although the above description is made about the case where zirconia ceramic powder is mixed with the crystallized glass, the invention can be applied to the case where zirconia ceramic powder may be replaced by alumina ceramic powder. In the case where alumina ceramic powder is used, a ceramic/crystallized glass composite having higher strength than that of a conventional composite produced by the conventional process can be produced. Alternatively, a mixture of zirconia ceramic powder and alumina ceramic powder may be used in this invention.

In the conventional process disclosed in the Japanese Patent Unexamined Publication No. Hei-1-115360, etc., a large amount of zirconia and/or alumina ceramic powder must be mixed with the glass. However, in the first aspect of the invention, the amount of zirconia and/or alumina ceramic powder mixed with the crystallized glass is not restricted specifically. The reason is as follows. Even in the case where the amount of zirconia and/or alumina ceramic powder is small, there is no risk of zirconia and/or alumina ceramic powder surrounded by fluidized glass and there is no risk of generation of pores in the vicinity of the boundary between the glass and the zirconia and/or alumina ceramic powder. Accordingly, a ceramic/crystallized glass composite of high strength having a zirconia and/or alumina ceramic skeleton can be obtained. It is a matter of course that when the amount of zirconia and/or alumina ceramic powder is large, a ceramic/crystallized glass comosite of high strength can be obtained.

However, when the amount of the crystallized glass is less than 5% by volume, the effect of addition of bioactivity by mixing with zirconia ceramic powder cannot be obtained in the resulting inorganic biomaterial. When the amount is more than 95%, on the contrary, the zirconia and/or alumina ceramic portion as a skeleton is so small that improvement of mechanical strength cannot be expected. Accordingly, the preferred range of the volume ratio of crystallized glass to zirconia and/or alumina ceramic is from 5:95 to 95:5. With respect to the material excellent in both bioactivity and strength, the more preferred range is from 40:60 to 90:10.

The fourth step is of preparing an inorganic biomaterial of a ceramics/crystallized glass composite by molding the mixture powder obtained by the third step into a desired shape and then heat-treating the resulting molding in a temperature range in which the partially stabilized zirconia and/or alumina powder is sintered.

In this step, the mixture powder of crystallized glass powder and zirconia and/or alumina ceramic powder is molded into a desired shape by a known molding method such as dust molding, cold isostatic molding (rubber press molding), injection molding, extrusion molding or the like. Then, the resulting molding is heat-treated within the sintering temperature range in which the zirconia and/or alumina ceramic powder is sintered. When the zirconia and/or alumina ceramic powder is sintered, there is no occurrence of fluidization/sintering of the glass. Accordingly, a fine and strong ceramic/crystallized glass composite can be obtained. The temperature range in which the zirconia and/or alumina ceramic powder is sintered can be found by measuring thermal contraction while heating the molding of the crystallized glass/zirconia and/or alumina ceramic powder mixture at a constant rate. In short, the range from the start temperature of thermal contraction to its end is taken as the sintering temperature range. For example, sintering of zirconia starts from about 800° C. In general, the temperature in which zirconia is sintered most densely is 1300° C. or more. However, when the temperature is higher than 1500° C., the crystallized glass portion is melted to generate pores or is made to react with zirconia ceramic powder to lose the bioactive function in some cases. Therefore, the preferred sintering temperature range is not higher than 1500° C. Recently, zirconia ceramics capable of being sintered densely at a relatively low temperature of 1000° to 1300° C. through adding a small amount of transition metal oxide such as zinc oxide, manganese oxide, copper oxide, cobalt oxide, nickel oxide, etc. have been developed [reference be made to "Zirconia Ceramics 9", Uchida Rokakuho Publishing Co. Ltd., Apr. 10, 1987, pp 1-12]. The melting point of the crystallized glass varies according to its composition. Accordingly, the melting of the crystallized glass may start at 1300° C. in some cases. The aforementioned zirconia ceramic powder capable of being sintered densely at a low temperature of 1000° to 1300° C. is suitable to these cases. A suitable known method can be used as the sintering method in the fourth step. When hot press method or HIP (hot isostatic pressing) method is used, sintering is accelerated so that the number of pores is reduced and, accordingly, a biomaterial showing larger mechanical strength can be obtained.

Next, the process for producing an inorganic biomaterial according to the second aspect of the invention will be explained successively the step by the step.

In the first step of the process according to the second aspect of the invention, crystals of calcium phosphate are heat-treated in the temperature range of from 800° to 1400° C. to prepare a calcium phosphate crystal sintered body. Examples of the crystals of calcium phosphate subjected to heat-treatment in the first step may be hydroxyapatite $[Ca_{10}(PO_4)_6(OH)_2]$, tricalcium phosphate $[Ca_3(PO_4)_2]$, octacalcium phosphate $[Ca_8H_2(PO_4)_6 \cdot 5H_2O]$, etc. These materials may be used singly or in combination selectively. As a method for producing crystals of calcium phosphate, any suitable method selected from a dry method and a wet method can be used. In general, the powder prepared by the wet method in which calcium phosphate is precipitated from an aqueous solution containing calcium and phosphoric acid, can be sintered more densely than the powder prepared by the dry method. Further, in the wet method, two or more kinds of calcium phosphate crystals can co-exist easily. Accordingly, calcium phosphate prepared by the wet method is preferably used in the second aspect of the invention. As described above, the heat-treating temperature to obtain a calcium phosphate crystal sintered body is restricted to a range of from 800° to 1400° C. The reason is as follows. When the temperature is lower than 800° C., a dense sintered body cannot be obtained. When the temperature is higher than 1400° C., on the contrary, the stability of the resulting sintered body is reduced.

In the second step, the calcium phosphate crystal sintered body obtained in the first step is ground to prepare powder. At the same time the powder is prepared or after the powder is prepared, the powder is mixed with partially stabilized zirconia and/or alumina ceramic powder. In the case where the grinding of the calcium phosphate crystal sintered body and the mixing with partially stabilized zirconia and/or alumina ceramic powder are carried out simultaneously, a known means such as a ball mill or the like can be used. Preferably, after the calcium phosphate sintered body is once ground to a particle size of 500 $\mu$m or less by a known means such as a ball mill, the resulting powder is mixed with partially stabilized zirconia and/or alumina ceramic powder by a known means such as a ball mill and ground together with the zirconia and/or alumina ceramic powder. It is preferable that the calcium phosphate crystal sintered body obtained by the simultaneous grinding or the two-stage grinding has a particle size of 75 $\mu$m or less. The reason is as follows. When the particle size of the calcium phosphate crystal sintered body in the finally produced composite ceramic biomaterial is larger than 75 $\mu$m, the sintered body is, in most cases, so defective that the mechanically high-strength composite ceramic biomaterial cannot be fabricated.

To make the particle size of the calcium phosphate crystal sintered body not larger than 75 $\mu$m, it is desirable that the particle size of the calcium phosphate crystal sintered body before mixing with partially stabilized zirconia and/or alumina ceramic powder in the second step is not larger than 500 $\mu$m. The reason is as follows. When particles larger than 500 $\mu$m exist in the calcium phosphate crystal sintered body, the particle size cannot be reduced so sufficiently that particles of the calcium phosphate crystal sintered body larger than 75 $\mu$m remain after mixing.

The partially stabilized zirconia and/or alumina powder used in the process according to the first aspect of the invention can be used as they are as the partially stabilized zirconia and/or alumina powder to be mixed with the calcium phosphate crystal sintered body in the second step of the process according to the second aspect of the invention. Accordingly, the details thereof are not described here.

According to the second aspect-of the invention, a high-strength composite ceramic biomaterial having zirconia and/or alumina ceramics as a skeleton can be produced even in the case where the amount of zirconia and/or alumina ceramic powder used in the second step is small. Of course, a high-strength composite ceramic biomaterial can be produced in the case where the amount of zirconia and/or alumina ceramic powder is large. However, when the amount of the calcium phosphate crystal is less than 5% by volume, the effect of addition of bioactivity by mixing with zirconia ceramic powder cannot be obtained in the resulting inorganic biomaterial. When the amount is more than 95%, the zirconia and/or alumina ceramic portion as a skeleton is so small that improvement of mechanical strength cannot be expected. Accordingly, the preferred range of the volume ratio of calcium phosphate crystal sintered body powder to zirconia and/or alumina ceramic powder is from 5:95 to 95:5. With respect to the material excellent in both bioactivity and strength, the more preferred range is from 40:60 to 90:10.

In the third step, the mixture powder obtained in the second step is molded into a desired shape and then the molding is sintered within the temperature range in which zirconia and/or alumina is sintered to thereby prepare a composite ceramic biomaterial.

In the third step, the mixture powder is molded by a known molding method such as dust pressing, cold isostatic pressing (rubber press molding), injection molding, extrusion molding, or the like. The temperature range in which the zirconia and/or alumina ceramic powder is sintered can be found by measuring thermal contraction while heating the molding of the mixture of calcium phosphate crystal sintered body powder and zirconia and/or alumina ceramic powder at a constant rate. In short, the range from the start temperature of thermal contraction to its end is taken as the sintering temperature range. For example, sintering of zirconia starts from about 800° C. In general, the temperature in which zirconia is sintered most densely is 1300° C. or more. However, when the temperature is higher than 1400° C., the calcium phosphate crystal sintered body powder is decomposed to produce pores or is made to react with zirconia ceramic powder to lose the bioactive function in some cases. Therefore, the preferred sintering temperature range is not higher than 1400° C. In the case of alumina, the preferred temperature range is not higher than 1500° C. Recently, zirconia ceramics capable of being sintered densely at a relatively low temperature in a range of from 1000° to 1300° C. through adding a small amount of transition metal oxide such as zinc oxide, manganese oxide, copper oxide, cobalt oxide, nickel oxide, etc. have been developed [reference be made to "Zirconia Ceramics 9", Uchida Rokakuho Publishing Co. Ltd., Apr. 10, 1987, pp 1–12]. For example, in some cases, the calcium phosphate crystal such as $\beta$-tricalcium phosphate is transformed at a low temperature in a range of from 1150° to 1300° C. The aforementioned zirconia ceramic powder capable of being sintered densely at a low temperature in a range of from 1000° to 1300° C. is suitable to these cases.

A suitable known method may be used as the heat-treating method for sintering. When hot press method or HIP (hot isostatic pressing) method is used, sintering is accelerated so that the number of pores is reduced and, accordingly, a biomaterial showing a larger mechanical strength can be obtained.

When calcium phosphate crystal fine powder and partially stabilized zirconia fine powder are mixed and sintered by the conventional process according to the Japanese Patent Unexamined Publication No. Sho-64-18973, the following disadvantages arise. When the temperature reach a value in which calcium phosphate powder is sintered, (1) calcium phosphate is sintered to thereby surround the partially stabilized zirconia powder, or (2) reaction between calcium phosphate fine powder and zirconia fine powder is made easily in the boundary, so that pores are generated or the partially stabilized zirconia is stabilized fully in most cases. These phenomena occur particularly in the case where the amount of the partially stabilized zirconia powder is small.

A calcium phosphate crystal such as apatite starts sintering at about 600° C. and is stable till about 1400° C. The degree of sintering can be judged from measurement of thermal contraction of the calcium phosphate crystal. The stability of the crystal can be judged from X-ray diffraction after heat-treatment. At 600° C., sintering is not progressed so that a dense sintered body cannot be obtained. At 800° C., a dense calcium phosphate sintered body can be obtained.

According to the second aspect of the invention, the calcium phosphate crystal is sintered at the temperature range of from 800° to 1400° C. in the first step, so that a dense and stable calcium phosphate crystal sintered body can be produced. The calcium phosphate crystal sintered body thus once densely sintered is not enough to sinter densely again even if the sintered body is ground to a particle size of 50 μm and then subjected to heat-treatment. Accordingly, the calcium phosphate crystal once densely sintered is not sintered again, even though it is treated as follows: the calcium phosphate crystal once already sintered is ground to prepare powder in the second step; the powder is mixed with zirconia powder and/or alumina powder simultaneously with or after the grinding thereof; the mixture is further ground to prepare mixture powder; and then the mixture powder is subjected to sintering in the third step within the temperature range in which zirconia and/or alumina is sintered. Therefore, the above-mentioned disadvantage of (1) can be eliminated. The particle size of the calcium phosphate crystal sintered body powder obtained by grinding is not reduced excessively. Therefore, the above-mentioned disadvantage of (2) can be eliminated.

Figure 3:
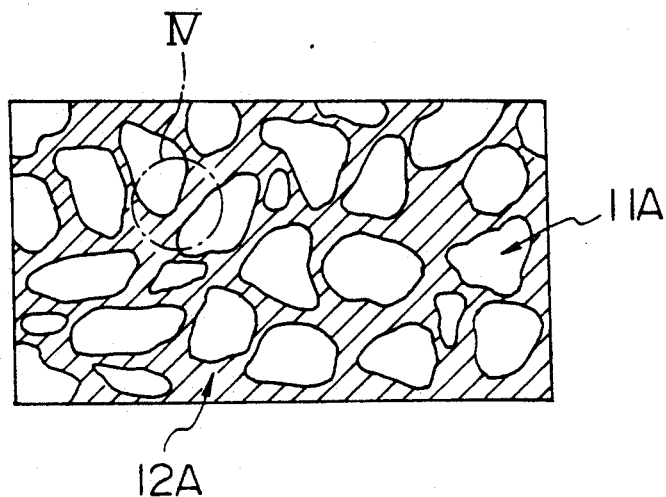
FIG. 3 is a typical view showing the structure of a composite ceramic biomaterial obtained according to the second aspect of the invention.
Figure 4:
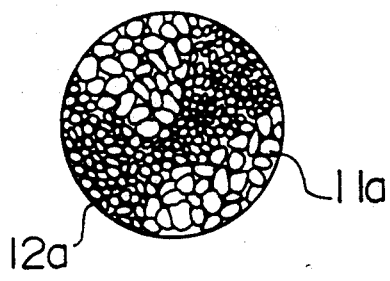
FIG. 4 is an enlarged view showing a circular portion IV in FIG. 3.
Figure 5:
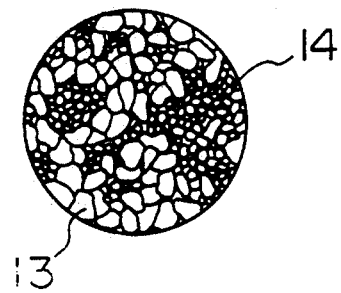
FIG. 5 is a typical enlarged view showing the structure of a conventional composite ceramic biomaterial.

The result of observation, by using an electron microscope, of the inorganic biomaterial produced according to the second aspect of the invention is shown typically in FIGS. 3 and 4. As shown in FIG. 3 and FIG. 4 which is an enlarged view of the circular portion IV in FIG. 3, the inorganic biomaterial obtained according to the second aspect of the invention has a plurality of first sintered portions 11A constituted by crystals of calcium phosphate 11a, and a plurality of second sintered portions 12A constituted by crystals of partially stabilized zirconia and/or alumina 12a, the plurality of first sintered portions being shaped like islands, the plurality of second sintered portions being shaped like an island-studded sea. In short, the plurality of first sintered portions 11A constituted by crystals of calcium phosphate 11a excellent in biocompatibility are dispersed in the high-strength second sintered portions 12A, as a skeleton, constituted by crystals of partially stabilized zirconia and/or alumina 12a. Consequently, the inorganic biomaterial is improved in biocompatibility and strength.

EXAMPLES

The present invention will be described more in detail hereunder with respect to various Examples. However, the present invention is not limited to these Examples.

Examples according to the First Aspect of the Invention

Example 1

Using oxides, carbonates, phosphates, hydrates, fluorides, etc. as raw materials, there was prepared a batch of glass materials to form glass containing 47.8% by weight of CaO, 44.0% by weight of $SiO_2$, 1.5% by weight of MgO, 6.5% by weight of $P_2O_5$ and 0.2% by weight of fluorine ($F_2$). The batch was placed in a platinum crucible and melted at 1550° C. for 2 hours. The melt was poured into water to prepare glass (the first step). The glass was dried. The dried glass was heated from room temperature to 1200° C. at a constant rate of 3° C./min in an electric furnace and then was kept at 1200° C. for 2 hours to thereby crystallize the glass (the second step). The crystallized glass was placed in a ball mill and ground to a particle size of 500 μm or less. The crystallized glass powder obtained above and partially stabilized zirconia ceramic powder (mean particle diameter: 0.3 μm) prepared by a coprecipitation method and containing 2.5 mol % of $Y_2O_3$ were placed in a ball mill in various ratios, wet-mixed for several hours while the particle size of the crystallized glass was reduced to 75 μm or less, and then dried (the third step). Each of the resulting mixtures was placed in a graphite mold, heated from room temperature to 1300° C. at a constant rate of 3° C./min while applying pressure of 30 MPa and kept at 1300° C. for 2 hours, by which the molding was sintered. Then, the molding was cooled to a room temperature in a furnace. Thus, various zirconia ceramic/crystallized glass composites were prepared (the fourth step). Each of the zirconia ceramic/crystallized glass composites had a relative density of 97% or more, so that the number of pores was very small. The zirconia ceramic/crystallized glass composites were ground and, using the resulting powders, the crystalline phases precipitated in the glass of each composite were identified according to the method of powder X-ray diffraction. In all the composites, crystals of apatite and wollastonite were precipitated. On the other hand, each composite was formed into a shape of a 3×4×36 mm rectangular pillar and subjected to three-point bending strength test according to the method of JIS R1601. The relationships between zirconia ceramic content (percentage by volume) and three-point bending strength, of the composites are shown in the curve 1 in FIG. 1. The curve 2 in FIG. 1 shows the relationships between zirconia ceramic content and three-point bending strength, of inorganic biomaterials prepared by the conventional process disclosed in the Japanese Patent Unexamined Publication No. Hei-1-115360. As is clear from FIG. 1, the inorganic biomaterials of this Example showed higher bending strength than that of the conventional inorganic biomaterials and, particularly, the inorganic biomaterials of this Example showed higher strength even when the zirconia content was small.

Example 2

Figure 2:
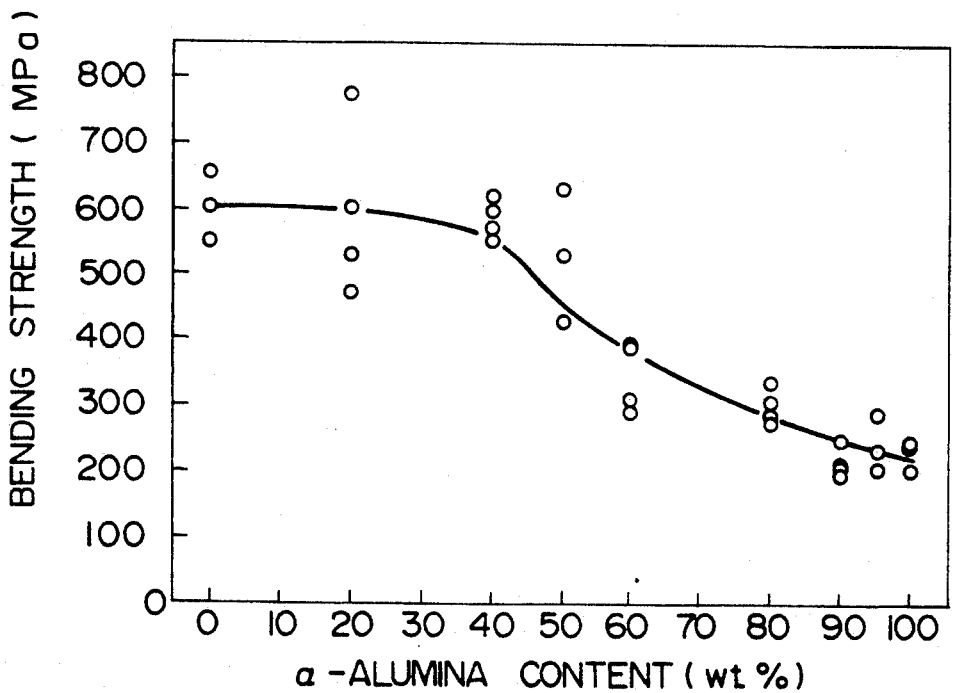
FIG. 2 is a graph showing the relationship between α-alumina content (percentage by weight) in zirconia ceramic and bending strength, of a zirconia ceramic/crystallized glass composite obtained according to the first aspect of the invention.

Using oxides, carbonates, phosphates, hydrates, fluorides, etc. as raw materials, there was prepared a batch of glass materials to form glass containing 47.8% by weight of CaO, 44.0% by weight of $SiO_2$, 1.5% by weight of MgO, 6.5% by weight of $P_2O_5$ and 0.2% by weight of fluorine ($F_2$). The batch was placed in a platinum crucible and melted at 1550° C. for 2 hours. The melt was poured into water to prepare glass (the first step). The glass was dried. The dried glass was heated from room temperature to 1200° C. at a constant rate of 3° C./min in an electric furnace and then was kept at 1200° C. for 2 hours to thereby crystallize the glass (the second step). The crystallized glass was placed in a ball mill and ground to a particle size of 500 μm or less. The crystallized glass powder obtained above and partially stabilized zirconia ceramic powder (mean particle diameter: 0.3 μm) prepared by a coprecipitation method and containing 2.5 mol % of $Y_2O_3$ and α-alumina in various ratios were placed in a ball mill in a volume ratio of 70 (crystallized glass): 30 (partially stabilized zirconia ceramic powder). They were wet-mixed in the ball mill for several hours while reducing the particle size of the crystallized glass to 75 μm or less and then dried (the third step). Each of the resulting mixtures was placed in a graphite mold, heated from room temperature to 1350° C. at a constant rate of 3° C./min while applying pressure of 30 MPa and kept at 1350° C. for 2 hours, by which the molding was crystallized and sintered. Then, the molding was cooled to a room temperature in a furnace. Thus, various zirconia ceramic/crystallized glass composites different in the α-alumina content (percentage by weight) of the zirconia ceramic were prepared (the fourth step). Each of the zirconia ceramic/crystallized glass composites had a relative density of 96% to 99%, so that the number of pores was very small. The zirconia ceramic/crystallized glass composites were ground, and, using the resulting powders, the crystalline phases precipitated in the glass of each composite were identified according to the method of powder X-ray diffraction. In all the composites, crystals of apatite and wollastonite were precipitated. On the other hand, each composite was formed into a shape of a 3×4×36 mm rectangular pillar and subjected to three-point bending strength test according to the method of JIS R1601. The relationships between α-alumina content (percentage by volume) of zirconia ceramic and three-point bending strength, of the composites are shown in FIG. 2. As is clear from FIG. 2, the inorganic biomaterials of this Example had higher bending strength than that of the conventional inorganic biomaterials.

Example 3

Using oxides, carbonates, phosphates, hydrates, fluorides, etc. as raw materials, a batch of glass materials was prepared. The batch was placed in a platinum crucible and melted at a temperature of 1450° C. to 1550° C. for 2 hours. The melt was poured into water. Thus, 32 glass samples respectively having compositions as shown in Table 1 were prepared (the first step). Each of the glass samples was dried. The dried glass sample was heated from room temperature to 1200° C. at a constant rate of 3° C./min in an electric furnace and then was kept at 1200° C. for 2 hours to thereby crystallize the glass (the second step). The crystallized glass was placed in a ball mill and ground to a particle size of 500 μm or less. The crystallized glass powder with the particle size of 500 μm or less and partially stabilized zirconia ceramic powder (mean particle diameter: 0.6 μm) prepared by a coprecipitation method and containing 2.6 mol % of $Y_2O_3$ and 0.3 mol % of ZnO were placed in a ball mill in a volume ratio of 70 (crystallized glass powder): 30 (partially stabilized zirconia ceramic powder). They were wet-mixed in the ball mill for several hours while reducing the particle size of the crystallized glass to 75 μm or less and then dried (the third step). Each of the resulting mixtures was shaped like a 50 mm φ disc by using a mold, heated in the electric furnace from room temperature to 1200° C. at a constant rate of 3° C./min, kept at 1200° C. for 2 hours and cooled to room temperature in the furnace to prepare a preliminary sintered body. The preliminary sintered body was heated from a room temperature to 1200° C. at a constant rate of 3° C./min while applying pressure of 200 MPa in an atmosphere of argon gas and then kept at 1200° C. for 2 hours, by which the compact was molded by using hot isostatic pressing (HIP). The molding was cooled to a room temperature in the furnace. Thus, various zirconia ceramic/crystallized glass composites were prepared (the fourth step). Each of the zirconia ceramic/crystallized glass composites had a relative density of 98.5% or more, so that the number of pores was very small. The zirconia ceramic/crystallized glass composites were ground and, using the resulting powders, the crystalline phases precipitated in the glass of each composite were identified according to the method of powder X-ray diffraction. In the composites, crystals as shown in Table 1 were precipitated. On the other hand, each composite was formed into a shape of a 3×4×36 mm rectangular pillar and subjected to three-point bending strength test according to the method of JIS R1601.

The glass compositions, the crystalline phases precipitated in the glass of each composite, and the three-point bending strength is shown in Table 1. As is clear from Table 1, the 32 kinds of inorganic biomaterials of this Example containing a small quantity of zirconia showed higher bending strength than that of the conventional inorganic biomaterials.

TABLE 1

| No. | 1 | 2 | 3 |
|---|---|---|---|
| Glass composition (wt %) | | | |
| CaO | 47.5 | 49.2 | 23.2 |
| $P_2O_5$ | 14.0 | 1.0 | 27.0 |
| $SiO_2$ | 38.5 | 49.8 | 49.8 |
| Others | | | |
| Crystalline phases precipitated in the glass | Apatite Wollastonite | Apatite Wollastonite | Apatite Wollastonite Tricalcium-phosphate |
| Bending strength (MPa) | 520 | 520 | 520 |

| No. | 4 | 5 | 6 |
|---|---|---|---|
| Glass composition (wt %) | | | |
| CaO | 55.6 | 44.7 | 36.3 |
| $P_2O_5$ | 22.0 | 16.3 | 16.3 |
| $SiO_2$ | 22.4 | 34.2 | 35.4 |
| Others | | MgO 4.6 $F_2$ 0.2 | MgO 11.5 $F_2$ 0.5 |
| Crystalline phases precipitated in the glass | Apatite Wollastonite | Apatite Wollastonite Diopside | Apatite Diopside |
| Bending strength (MPa) | 520 | 600 | 550 |

| No. | 7 | 8 | 9 |
|---|---|---|---|
| Glass composition (wt %) | | | |
| CaO | 26.8 | 24.6 | 26.1 |
| $P_2O_5$ | 14.1 | 16.0 | 23.0 |
| $SiO_2$ | 34.1 | 28.7 | 29.8 |
| Others | MgO 11.5 $Al_2O_3$ 12.5 $F_2$ 0.8 | MgO 30.7 | MgO 18.6 $F_2$ 0.5 $Li_2O$ 2.0 |
| Crystalline phases precipitated in the glass | Apatite Anorthite Diopside Forsterite Tricalcium-phosphate | Apatite Forsterite Diopside Tricalcium-phosphate | Apatite Akermanite Diopside Tricalcium-phosphate |
| Bending strength (MPa) | 650 | 550 | 520 |

| No. | 10 | 11 | 12 |
|---|---|---|---|
| Glass composition | | | |

TABLE 1-continued

| (wt %) | | | | | | |
|---|---|---|---|---|---|---|
| CaO | | 16.6 | | 47.4 | | 47.4 |
| $P_2O_5$ | | 16.2 | | 6.2 | | 6.2 |
| $SiO_2$ | | 37.2 | | 42.2 | | 42.2 |
| Others | MgO | 29.5 | $Y_2O_3$ | 2.0 | MgO | 2.0 |
| | $F_2$ | 0.5 | $ZrO_2$ | 2.0 | $Ta_2O_5$ | 2.0 |
| | | | $F_2$ | 0.5 | $F_2$ | 0.2 |
| Crystalline phases precipitated in the glass | Apatite Diopside Forsterite | | Apatite Wollastonite | | Apatite Wollastonite | |
| Bending strength (MPa) | 600 | | 650 | | 600 | |

| No. | 13 | 14 | 15 |
|---|---|---|---|
| Glass composition (wt %) | | | |
| CaO | 48.3 | 47.9 | 48.3 |
| $P_2O_5$ | 6.3 | 6.3 | 6.3 |
| $SiO_2$ | 43.2 | 42.6 | 43.2 |
| Others | $F_2$ 0.2 | $F_2$ 0.2 | $F_2$ 0.2 |
| | $TiO_2$ 2.0 | $K_2O$ 3.0 | SrO 2.0 |
| Crystalline phases precipitated in the glass | Apatite Wollastonite | Apatite Wollastonite | Apatite Wollastonite |
| Bending strength (MPa) | 600 | 510 | 510 |

| No. | 16 | 17 | 18 |
|---|---|---|---|
| Glass composition (wt %) | | | |
| CaO | 48.3 | 48.3 | 48.3 |
| $P_2O_5$ | 6.3 | 6.3 | 6.3 |
| $SiO_2$ | 43.2 | 43.2 | 43.2 |
| Others | $F_2$ 0.2 | MgO 0.2 | $F_2$ 0.2 |
| | $Nb_2O_5$ 2.0 | $Na_2O$ 2.0 | $B_2O_3$ 2.0 |
| Crystalline phases precipitated in the glass | Apatite Wollastonite | Apatite Wollastonite | Apatite Wollastonite |
| Bending strength (MPa) | 510 | 501 | 520 |

| No. | 19 | 20 | 21 |
|---|---|---|---|
| Glass composition (wt %) | | | |
| CaO | 49.3 | 47.8 | 12.0 |
| $P_2O_5$ | 6.5 | 6.5 | 15.5 |
| $SiO_2$ | 44.0 | 44.0 | 47.7 |
| Others | $F_2$ 0.2 | MgO 1.5 | $Al_2O_3$ 24.8 |
| | | $F_2$ 0.2 | |
| Crystalline phases precipitated in the glass | Apatite Wollastonite | Apatite Wollastonite | Apatite Anorthite Tricalcium-phosphate |
| Bending strength (MPa) | 550 | 650 | 620 |

| No. | 22 | 23 | 24 |
|---|---|---|---|
| Glass composition (wt %) | | | |
| CaO | 45.0 | 45.0 | 45.0 |
| $P_2O_5$ | 6.0 | 6.0 | 6.0 |
| $SiO_2$ | 39.0 | 39.0 | 39.0 |
| Others | $K_2O$ 9.5 | $Li_2O$ 9.5 | $Na_2O$ 9.5 |
| | $F_2$ 0.5 | $F_2$ 0.5 | $F_2$ 0.5 |
| Crystalline phases precipitated in the glass | Apatite Wollastonite Tricalcium-phosphate | Apatite Wollastonite Tricalcium-phosphate | Apatite Wollastonite Tricalcium-phosphate |
| Bending strength (MPa) | 510 | 510 | 510 |

| No. | 25 | 26 | 27 |
|---|---|---|---|
| Glass composition (wt %) | | | |
| CaO | 45.0 | 45.0 | 45.0 |
| $P_2O_5$ | 6.0 | 6.0 | 6.0 |
| $SiO_2$ | 39.0 | 39.0 | 39.0 |
| Others | $TiO_2$ 9.5 | $ZrO_2$ 9.5 | SrO 9.5 |
| | $F_2$ 0.5 | $F_2$ 0.5 | $F_2$ 0.5 |
| Crystalline phases precipitated in the glass in the glass | Apatite Wollastonite Tricalcium-phosphate | Apatite Wollastonite Tricalcium-phosphate | Apatite Wollastonite Tricalcium-phosphate |
| Bending strength (MPa) | 600 | 650 | 600 |

| No. | 28 | 29 | 30 |
|---|---|---|---|
| Glass composition (wt %) | | | |
| CaO | 45.0 | 45.0 | 45.0 |
| $P_2O_5$ | 6.0 | 6.0 | 6.0 |
| $SiO_2$ | 39.0 | 39.0 | 39.0 |
| Others | $Nb_2O_5$ 9.5 | $Ta_2O_5$ 9.5 | $B_2O_3$ 9.5 |
| | $F_2$ 0.5 | $F_2$ 0.5 | $F_2$ 0.5 |
| Crystalline phases precipitated in the glass | Apatite Wollastonite Tricalcium-phosphate | Apatite Wollastonite Tricalcium-phosphate | Apatite Wollastonite Tricalcium-phosphate |
| Bending strength (MPa) | 600 | 580 | 580 |

| No. | 31 | 32 |
|---|---|---|
| Glass composition (wt %) | | |
| CaO | 45.0 | 45.0 |
| $P_2O_5$ | 6.0 | 6.0 |
| $SiO_2$ | 44.5 | 44.0 |
| Others | $F_2$ 4.5 | $Y_2O_3$ 5.0 |
| Crystalline phases precipitated in the glass | Apatite Wollastonite | Apatite Wollastonite |
| Bending strength (MPa) | 620 | 630 |

(Note) In the item of "Glass composition", "$F_2$" is shown with a converted value of "$F_2$" of fluorine in the glass composition.

Example 4

Using oxides, carbonates, phosphates, hydrates, fluorides, etc. as raw materials, there was prepared a batch of glass materials to form glass containing 47.8% by weight of CaO, 44.0% by weight of $SiO_2$, 1.5% by weight of MgO, 6.5% by weight of $P_2O_5$ and 0.2% by weight of fluorine ($F_2$). The batch was placed in a platinum crucible and melted at 1550° C. for 2 hours. The melt was poured into water to prepare glass (the first step). The glass was dried. The dried glass was heated from room temperature to 1200° C. at a constant rate of 3° C./min in an electric furnace and then was kept at 1200° C. for 2 hours to thereby crystallize the glass (the second step). The crystallized glass was placed in a ball mill and ground to a particle size of 500 μm or less. The crystallized glass powder obtained above and α-alumina ceramic powder (mean particle diameter:0.2 μm) were placed in a ball mill in a volume ratio of 60 (crystallized glass): 40 (α-alumina ceramic powder). They were wet-mixed in the ball mill for several hours while reducing the particle size of the crystallized glass to 75 μm or less and then dried (the third step). The molding was placed in a graphite mold, heated from a room temperature to 1350° C. at a constant rate of 3° C./min while applying pressure of 30 MPa and then was kept at 1350° C. for 2 hours, by which the molding was crystallized and sintered. Then, the molding was cooled to a room temperature in a furnace. Thus, an alumina ceramic/crystallized glass composite was prepared (the fourth step). The alumina ceramic/crystallized glass composite had a relative density of 96%. The alumina ceramic/crystallized glass composite was ground, and, using the resulting powder, the crystalline phase precipitated in the glass of the composite was identified according to the method of powder X-ray diffraction. In the composite, crystals of apatite and wollastonite were precipitated.

On the other hand, the composite was formed into a shape of a 3×4×36 mm rectangular pillar and subjected to three-point bending strength test according to the method of JIS R1601. The three-point bending strength of the composite was 370 MPa.

Examples according to the Second Aspect of the Invention

Example 5

An aqueous solution containing 0.5 mol/l of Ca($NO_3$)$_2$ and an aqueous solution containing 0.5 mol/l of $(NH_4)_2HPO_4$ were made to react with each other at a temperature in a range of from 80° to 90° C. for 24 hours while mixing and stirring. If necessary, an aqueous solution containing 0.1 mol/l of NaOH was added dropwise to the resulting solution to adjust pH in a range from 7 to 10. The precipitated product was dried, subjected to rubber press molding under pressure of 196 MPa, heated from a room temperature to 1300° C. at a constant rate of 3° C./min in an electric furnace and kept at 1300° C. for 2 hours to prepare a calcium phosphate crystal sintered body (the first step). The sintered body was identified according to the method of powder X-ray diffraction. As the result of the powder X-ray diffraction, it was found that the sintered body consists of apatite and β-tricalcium phosphate. The calcium phosphate crystal sintered body obtained in the first step was placed in a ball mill and ground to a particle size of 500 μm or less. The calcium phosphate crystal sintered body powder obtained above and zirconia ceramic powder (partially stabilized zirconia, mean particle diameter:0.3 μm) prepared by a coprecipitation method and containing 3 mol % of $Y_2O_3$ were placed in a ball mill in various ratios. They were wet-mixed in the ball mill for several hours and then dried (the second step). The mixture obtained by the second step was placed in a graphite mold, heated from a room temperature to 1300° C. at a constant rate of 3° C./min while applying pressure of 30 MPa and then kept at 1300° C. for 2 hours, by which the molding was sintered. Then, the molding was cooled to a room temperature in a furnace. Thus, various composite ceramic biomaterials were prepared (the third step).

Figure 6:
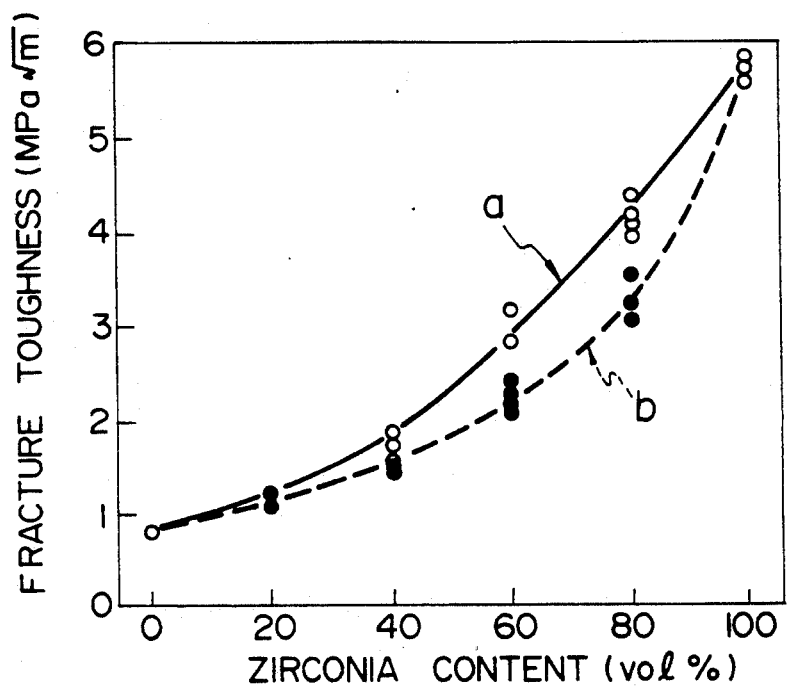
FIG. 6 is a graph showing the relationship between zirconia content (percentage by volume) and fracture toughness, of a composite ceramic biomaterial obtained according to the second aspect of the invention.

Each of the composite ceramic biomaterials had a relative density of 97% to 98%. Each of the composite ceramic biomaterials was observed using an electron microscope. As the result of the observation, each structure of the biomaterials was shown in FIGS. 3 and 4. Further, each composite ceramic biomaterial was cut and mirror polished. Then, a Vickers indenter was pressed into the mirror surface of each biomaterial with 9.8N for 15 seconds. To calculate fracture toughness, the length of a crack extending from the pressed point was measured. The relationships between zirconia powder content (percentage by volume) and fracture toughness, of the composite ceramic biomaterials of this Example are shown in the curve a in FIG. 6. The curve b in FIG. 6 shows the fracture toughness of conventional composite ceramic biomaterials produced according to the Japanese Patent Unexamined Publication No. Sho-64-18973. As is clear from FIG. 6, the composite ceramic biomaterials of this Example had higher fracture toughness than those of the conventional biomaterials.

Example 6

An aqueous solution containing 0.5 mol/l of Ca($NO_3$)$_2$ and an aqueous solution containing 0.2 mol/l of $(NH_4)_2HPO_4$ were made to react with each other at a temperature in a range of 80° to 90° C. for 24 hours while mixing and stirring. If necessary, an aqueous solution containing 0.1 mol/l of NaOH was added dropwise to the resulting solution to adjust pH in a range from 7 to 8.5. The precipitated reaction product was dried, subjected to rubber press molding under pressure of 196 MPa, heated from a room temperature to 1300° C. at a constant rate of 3° C./min in an electric furnace and kept at 1300° C. for 2 hours to prepare a calcium phosphate crystal sintered body (the first step). The sintered body was identified according to the method of powder X-ray diffraction. As the result of the powder X-ray diffraction, it was found that the sintered body consists of apatite. The calcium phosphate crystal sintered body obtained by the first step was placed in a ball mill and ground to a particle size of 500 μm or less. The calcium phosphate crystal sintered body powder obtained above and zirconia ceramic powder (partially stabilized zirconia, mean particle diameter: 0.3 μm) prepared by a coprecipitation method and containing 3 mol % of $Y_2O_3$ and α-alumina in various ratios were placed in a ball mill in a volume ratio of 70 (calcium phosphate crystal sintered body powder): 30 (partially stabilized zirconia powder). They were wet-mixed in the ball mill for several hours and then dried (the second step). The mixture obtained by the second step was placed in a graphite mold, heated from a room temperature to 1350° C. at a constant rate of 3° C./min while applying pressure of 30 MPa and then kept at 1350° C. for 2 hours, by which the molding was sintered. Then, the molding was cooled to a room temperature in a furnace. Thus, various composite ceramic biomaterials were prepared (the third step).

Figure 7:
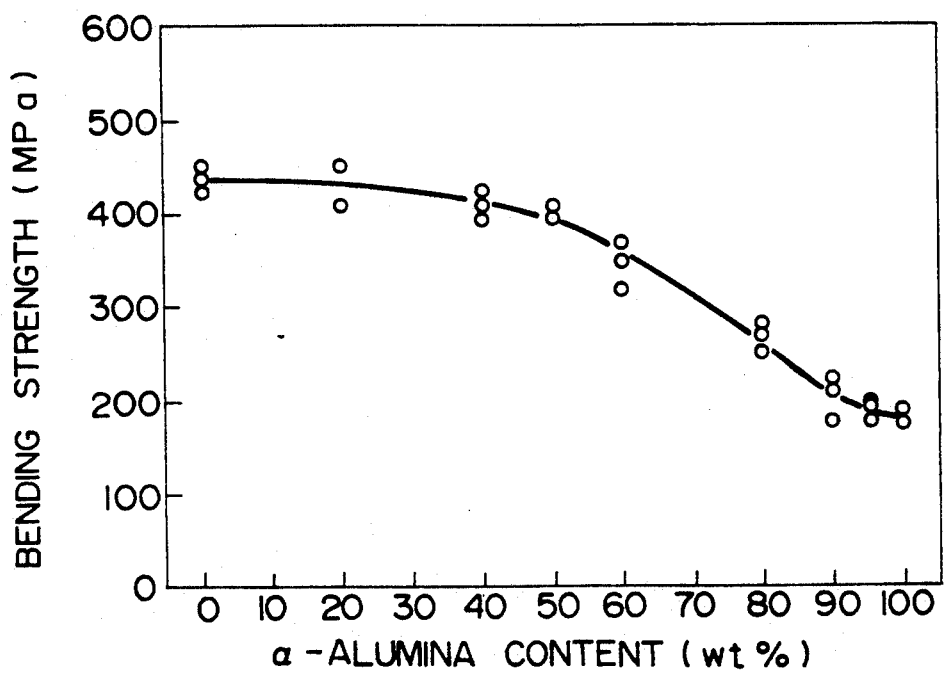
FIG. 7 is a graph showing the relationship between α-alumina content (percentage by weight) in zirconia ceramics and bending strength obtained according to the second aspect of the invention.

Each of the composite ceramic biomaterials had a relative density of 96% to 99%. Each of the composite ceramic biomaterials was observed using an electron microscope. As the result of the observation, each structure of the biomaterials was shown in FIGS. 3 and 4. Further, each composite ceramic biomaterial was ground to identify precipitated crystals according to the method of powder X-ray diffraction. As the result of the powder X-ray diffraction, crystals of apatite did not change. Further, tetragonal crystals of zirconia, cubic crystals of zirconia and α-alumina (only in the niomaterial containing α-alumina) could be identified. On the other hand, each composite ceramic biomaterial was formed into a shape of a 3×4×36 mm rectangular pillar and subjected to three-point bending strength test according to the method of JIS R1601. The relationships between α-alumina content (percentage by volume) of zirconia ceramic and three-point bending strength, of the biomaterials are shown in FIG. 7. As is clear from FIG. 7, the composite ceramic biomaterials of this Example had higher bending strength.

Example 7

An aqueous solution containing 0.5 mol/l of Ca($NO_3$)$_2$ and an aqueous solution containing 0.2 mol/l of $(NH_4)_2HPO_4$ were made to react with each other at a temperature of 80° to 90° C. for 24 hours while mixing and stirring. An aqueous solution containing 0.1 mol/l of NaOH was added dropwise to the resulting solution to obtain solutions respectively adjusted to pH 6.0, 6.8, 7.0, 8.0 and 9.0. The precipitated reaction product was dried, subjected to rubber press molding under pressure of 196MPa, heated from a room temperature to 1300° C. at a constant rate of 3° C./min in an electric furnace and kept at 1300° C. for 2 hours to prepare a calcium phosphate crystal sintered body (the first step). The sintered body was identified according to the method of powder X-ray diffraction. The result of the powder X-ray diffraction is shown in Table 2.

TABLE 2

| No. | 41 | 42 | 43 |
|---|---|---|---|
| pH at the time of forming crystals of calcium phosphate | 6.0 | 6.8 | 7.0 |
| Crystalline phases of calcium phosphate sintered body | Octacalcium phosphate | Octacalcium phosphate Hydroxyapatite | Hydroxyapatite Octacalcium phosphate β-tricalcium phosphate (a small amount) |
| Bending strength (MPa) | 330 | 350 | 350 |
| Fracture toughness (MPa√m) | 1.32 | 1.41 | 1.45 |

| No. | 44 | 45 |
|---|---|---|
| pH at the time of forming crystals of calcium phosphate | 8.0 | 9.0 |
| Crystalline phases of calcium phosphate sintered body | Hydroxyapatite | Hydroxyapatite β-tricalcium phosphate |
| Bending strength (MPa) | 400 | 420 |
| Fracture toughness (MPa√m) | 1.77 | 2.01 |

The calcium phosphate crystal sintered body was placed in a ball mill and ground to a particle size of 500 μm or less. The calcium phosphate crystal sintered body powder obtained above and zirconia ceramic powder (partially stabilized zirconia, mean particle diameter: 0.6 μm) prepared by a coprecipitation method and containing 2.6 mol % of $Y_2O_3$ and 0.3 mol % of ZnO were placed in a ball mill in a volume ratio of 70 (calcium phosphate crystal sintered body powder): 30 (zirconia powder). They were wet-mixed in the ball mill for several hours and then dried (second step). The mixture obtained by the second step was shaped like a 50 mm φ disk by using a mold, heated from room temperature to 1200° C. at a constant rate of 3° C./min in an electric furnace, kept at 1200° C. for 2 hours and then cooled to a room temperature in a furnace to prepare a preliminary sintered body. The preliminary sintered body was heated from a room temperature to 1200° C. at a constant rate of 3° C./min while applying pressure of 196MPa in an atmosphere of argon gas and then kept at 1200° C. for 2 hours, by which the body was molded by using hot isostatic pressing (HIP). The resulting molding was cooled to a room temperature in the furnace. Thus, composite ceramic biomaterials were prepared (the third step).

Each of the composite ceramic biomaterials had a relative density of 99% to 99.5%. Each of the composite ceramic biomaterials was observed using an electron microscope. As the result of the observation, each structure of the biomaterials was shown in FIGS. 3 and 4. Further, fracture toughness was calculated in the same method as in Example 5. Further, three-point bending strength was measured according to the method of JIS R1601. The measured calcium phosphate crystal phases, three-point bending strength and fracture toughness are shown in Table 2. As is clear from Table 2, the composite ceramic biomaterials of this Example had higher bending strength than that of the conventional calcium phosphate/zirconia composite sintered body even when the zirconia content in each biomaterials of this Example was small.

Example 8

An aqueous solution containing 0.5 mol/l of Ca(NO$_3$)$_2$ and an aqueous solution containing 0.5 mol/l of (NH$_4$)$_2$HPO$_4$ were made to react with each other at a temperature in a range of from 80° to 90° C. for 24 hours while mixing and stirring. If necessary, an aqueous solution containing 0.1 mol/l of NaOH was added dropwise to the resulting solution to adjust pH in a range from 7 to 10. The precipitated product was dried, subjected to rubber press molding under pressure of 196 MPa, heated from a room temperature to 1300° C. at a constant rate of 3° C./min in an electric furnace and kept at 1300° C. for 2 hours to prepare a calcium phosphate crystal sintered body (the first step). The sintered body was identified according to the method of powder X-ray diffraction. As the result of the powder X-ray diffraction, it was found that the sintered body consists of apatite and β-tricalcium phosphate. The calcium phosphate crystal sintered body obtained in the first step was placed in a ball mill and ground to a particle size of 500 μm or less. The calcium phosphate crystal sintered body powder obtained above and α-alumina powder (mean particle diameter: 0.2 μm) was placed in a ball mill in a volume ratio of 60 (calcium phosphate crystal sintered body powder):40 (α-alumina powder). They were wet-mixed in the ball mill for several hours and then dried (the second step). The mixture obtained in the second step was placed in a graphite mold, heated from a room temperature to 1350° C. at a constant rate of 3° C./min while applying pressure of 30 MPa and then kept at 1350° C. for 2 hours, by which the mixture was sintered. Then, the sintered mixture was cooled to a room temperature in a furnace. Thus, a composite ceramic biomaterial was prepared (the third step).

The composite ceramic biomaterial had a relative density of 96%. The composite ceramic biomaterial was observed using an electron microscope. As the result of the observation, the biomaterial had a structure as shown in FIGS. 3 and 4. Further, the composite ceramic biomaterial was formed into a shape of a 3×4×36 mm rectangular pillar and subjected to three-point bending strength test according to the method of JIS R1601. The three-point bending strength of the biomaterial was 270 MPa.

As described above in detail, according to the present invention, there can be obtained an inorganic biomaterial excellent in strength and biocompatibility, having a structure in which portions constituted by crystallized glass or crystals of calcium phosphate excellent in bioactivity are dispersed in a skeleton or matrix constituted by crystals of partially stabilized zirconia and/or alumina showing high strength. Accordingly, the inorganic biomaterial is very useful as a biomaterial for artificial bones, dental implants, etc.

What is claimed is:

1. A process for producing an inorganic biomaterial, which comprises:
    a first step of melting a mixture of glass raw materials and cooling it to thereby prepare glass containing the following components of the following proportions

| | |
|---|---|
| CaO | 12 to 56% by weight |
| $P_2O_5$ | 1 to 27% by weight |
| $SiO_2$ | 22 to 50% by weight |
| MgO | 0 to 34% by weight |
| $Al_2O_3$ | 0 to 25% by weight | in a total amount of at least 90%;

a second step of preparing crystallized glass by heat-treating the glass obtained in the first step in a temperature range in which there are precipitated a crystal of apatite and at least one crystal of alkaline earth metal silicate selected from the group consisting of wollastonite, diopside, forsterite, akermanite and anorthite;

a third step of preparing mixture powder by mixing the crystallized glass obtained by the second step with partially stabilized zirconia powder and/or alumina powder while grinding the crystallized glass or after grinding the crystallized glass; and a fourth step of preparing an inorganic biomaterial of a ceramics/crystallized glass composite by molding the mixture powder obtained by the third step into a desired shape and then heat-treating the resulting molding in a temperature range in which the partially stabilized zirconia and/or alumina powder is sintered.

2. A process according to claim 1, in which the mixture of glass raw materials further contains at least one component selected from the group consisting of $K_2O$, $Li_2O$, $Na_2O$, $TiO_2$, $ZrO_2$, SrO, $Nb_2O_5$, $Ta_2O_5$, $B_2O_3$, $Y_2O_3$ and fluorine ($F_2$), in an amount smaller than 10%.

3. A process according to claim 2, in which the amount of $Y_2O_3$ and the amount of fluorine are not larger than 5%, respectively.

4. A process according to claim 1, in which the particle size of the crystallized glass in the mixture powder obtained by the third step is 75 μm or less.

5. A process according to claim 1, in which the volume ratio of crystallized glass to zirconia and/or alumina ceramic powder is in a range of 5:95 to 95:5.

6. A process for producing an inorganic biomaterial, which comprises:

a first step of sintering a crystal of calcium phosphate at a temperature in a range of from 800° to 1400° C. to thereby prepare a calcium phosphate crystal sintered body;

a second step of grinding the sintered body obtained in the first step to thereby prepare powder of the sintered body, and, at the same time of or after preparation of the powder of the sintered body, mixing the prepared powder of the sintered body with partially stabilized zirconia powder and/or alumina powder to thereby prepare mixture powder; and a third step of molding the mixture powder obtained in the second step into a desired shape and heat-treating the resulting molding in a temperature range in which the partially stabilized zirconia and/or alumina powder is sintered.

7. A process according to claim 6, in which the crystal of calcium phosphate is constituted by at least one member selected from the group consisting of hydroxyapatite, tricalcium phosphate and octacalium phosphate.

8. A process according to claim 6, in which the particle size of the calcium phosphate crystal sintered body in the mixture powder obtained in the second step is 75 μm or less.

9. A process according to claim 6, in which the volume ratio of calcium phosphate crystal sintered body to zirconia and/or alumina ceramic powder is in a range of 5:95 to 95:5.

* * * * *